United States Patent [19]
Black

[11] Patent Number: 6,134,001
[45] Date of Patent: Oct. 17, 2000

[54] FLUID DIAGNOSTIC TECHNIQUE

[75] Inventor: John D. Black, Nr Ashbourne, United Kingdom

[73] Assignee: Rolls Royce PLC, Derby, United Kingdom

[21] Appl. No.: 09/280,977

[22] Filed: Mar. 30, 1999

[30] Foreign Application Priority Data

Apr. 4, 1998 [GB] United Kingdom .................... 9807220

[51] Int. Cl.[7] ....................................... G01D 3/30
[52] U.S. Cl. .......................... 356/318; 388/390; 388/393; 388/394
[58] Field of Search .................................... 356/318, 388, 356/390, 393, 394

[56] References Cited

U.S. PATENT DOCUMENTS 5,153,665  10/1992  Weinstein .
5,333,044   7/1994  Shaffer .

OTHER PUBLICATIONS

On the cooling of the plasma fireball produced by a laser spark in front of liquids and solids—D.Kaganovich et al., Phys. Plasmas 3 (2), Feb. 1996; 1996 American Institute of Physics.
Spectroscopic study of laser–produced plasmas in hydrogen, J. F. Kielkopf, vol. 52, No. 2, Physical–Review E. Aug. 1995.

Primary Examiner—Frank G. Font
Assistant Examiner—Reginald A. Ratliff
Attorney, Agent, or Firm—Pillsbury Madison & Sutro LLP

[57] ABSTRACT

A non-obstructive fluid diagnostic technique is described which enables the measurement of different parameters in a fluid. The diagnostic technique includes the steps of focusing a laser (10) in a fluid volume (14) to generate a laser induced breakdown spark (15). The characteristics of the initial laser induced breakdown spark (15) are measured and compared to the characteristics of a delayed image of the spark, formed by light emission due to recombination and excited molecules and ions generated by the laser induced spark (15). The differences between the initial and delayed images being used to diagnose characteristics of the fluid, such as velocity, temperature and pressure.

18 Claims, 3 Drawing Sheets

Fig.2.
Examples of Laser Induced Breakdown Images
Mass flow 0.6 kg s$^{-1}$ at 291 K
(a) Synchronous with laser pulse    (b) Delayed by 4.5µs
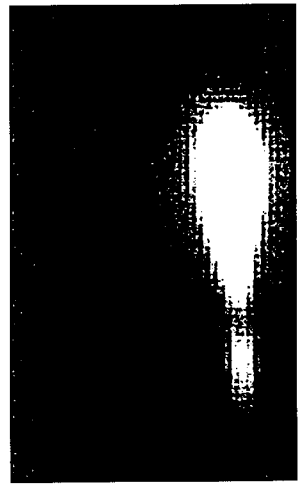 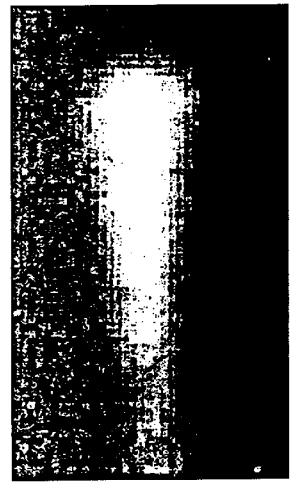
Flow direction from right to left.
Laser beam direction top to bottom of page.
The intensity of image (a) is ~15 x that of (b)
Shift of image centre in the flow direction = 11 pixels corresponding to 380 ms$^{-1}$.

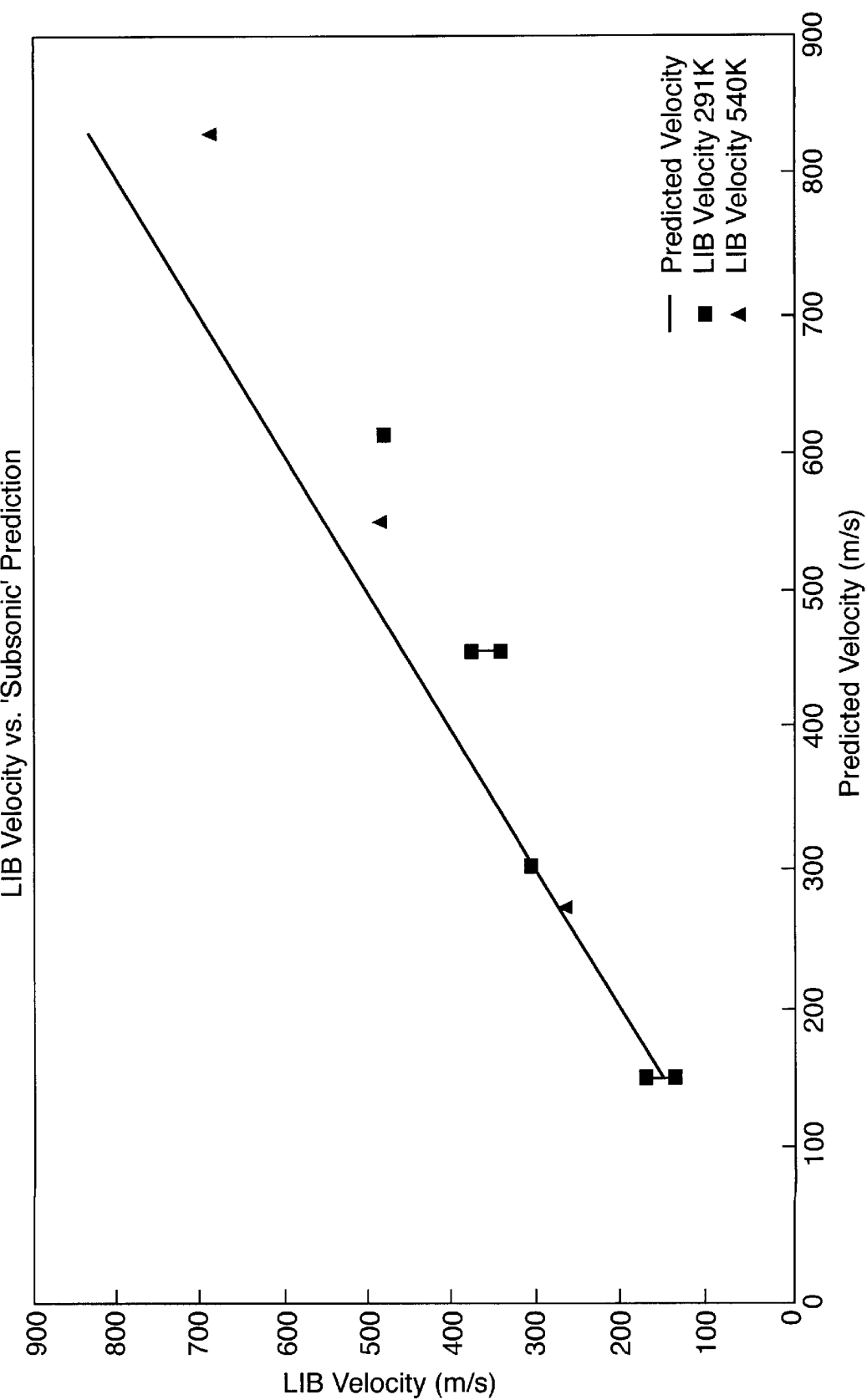

FLUID DIAGNOSTIC TECHNIQUE

BACKGROUND OF THE INVENTION

The present invention relates to fluid diagnostic techniques and in particular to non-obtrusive diagnostic techniques which enable the measurement of different parameters in a gas flow.

Optical techniques are desirable for the measurement of fluid parameters as other instruments, such as physical type probes, disturb the flow at precisely the location of measurement.

It is known to measure fluid parameters remotely using laser techniques. When a laser of sufficient power is focused tightly in a gas a small volume of the gas around the focus is ionized. This ionization, known as laser induced breakdown is accompanied by the emission of light and sound.

A considerable amount of light from the laser is scattered by the breakdown spark. Light emissions from recombination ions and electrons and from exited molecules and ions generated in the breakdown also persist after the initial laser pulse.

The present invention seeks to provide a non-intrusive diagnostic technique which utilizes the laser induced breakdown phenomenon.

According to a first embodiment of the present invention, a fluid diagnostic technique comprises the steps of focusing a laser in the fluid to generate a laser induced breakdown spark, measuring the characteristics of the initial laser induced breakdown spark and comparing the characteristics of the initial laser induced spark to the characteristics of a delayed image of the spark, formed by light emission due to recombination and excited molecules and ions generated by the laser induced spark, differences between the initial and delayed images being used to diagnose characteristics of the fluid.

In a second embodiment of the present invention, a fluid diagnostic technique for measuring the velocity of a fluid flow comprises the steps of focusing a laser in the fluid to generate an initial laser induced breakdown spark, measuring the center of the initial laser induced breakdown spark and comparing the center of the initial spark to the center of a delayed image of the spark formed by light emission due to recombination and exited molecules and ions generated by the initial laser induced spark, the shift in position of the center of the initial spark and the center of the delayed image of the spark being used to calculate the velocity of the fluid flow.

In a further embodiment of the present invention, a fluid diagnostic technique for measuring the temperature of a fluid comprises the steps of focusing a laser in a fluid to generate an initial laser induced breakdown spark, comparing the initial laser induced breakdown spark to a delayed image of the spark formed by the light emission due to recombination and excited molecules and ions generated by the initial laser breakdown spark, the rate of increase of the light emitting volume around the delayed image of the spark being used to calculate the temperature of the fluid.

Preferably a high power laser such as a Neodymium/YAG laser is used to generate the laser induced breakdown spark. The laser may be focused with a lens and preferably a camera is used to record the images of the laser induced breakdown spark so that the images can be compared.

A collection lens at 90° to the laser beam may be used to collect light emitted by the laser induced breakdown spark. The initial spark and the delayed image of the spark are separated by a time interval of the order of 4.5 $\mu$s.

BRIEF DESCRIPTION OF THE DRAWINGS

FIG. 2 shows examples of the recorded images of laser induced breakdown sparks recorded at 4.5 $\mu$s intervals.

FIG. 3 is a plot showing the correlation between the calculated velocity and the subsonic prediction.

DETAILED DESCRIPTIONS OF THE PREFERRED EMBODIMENTS

Figure 1:
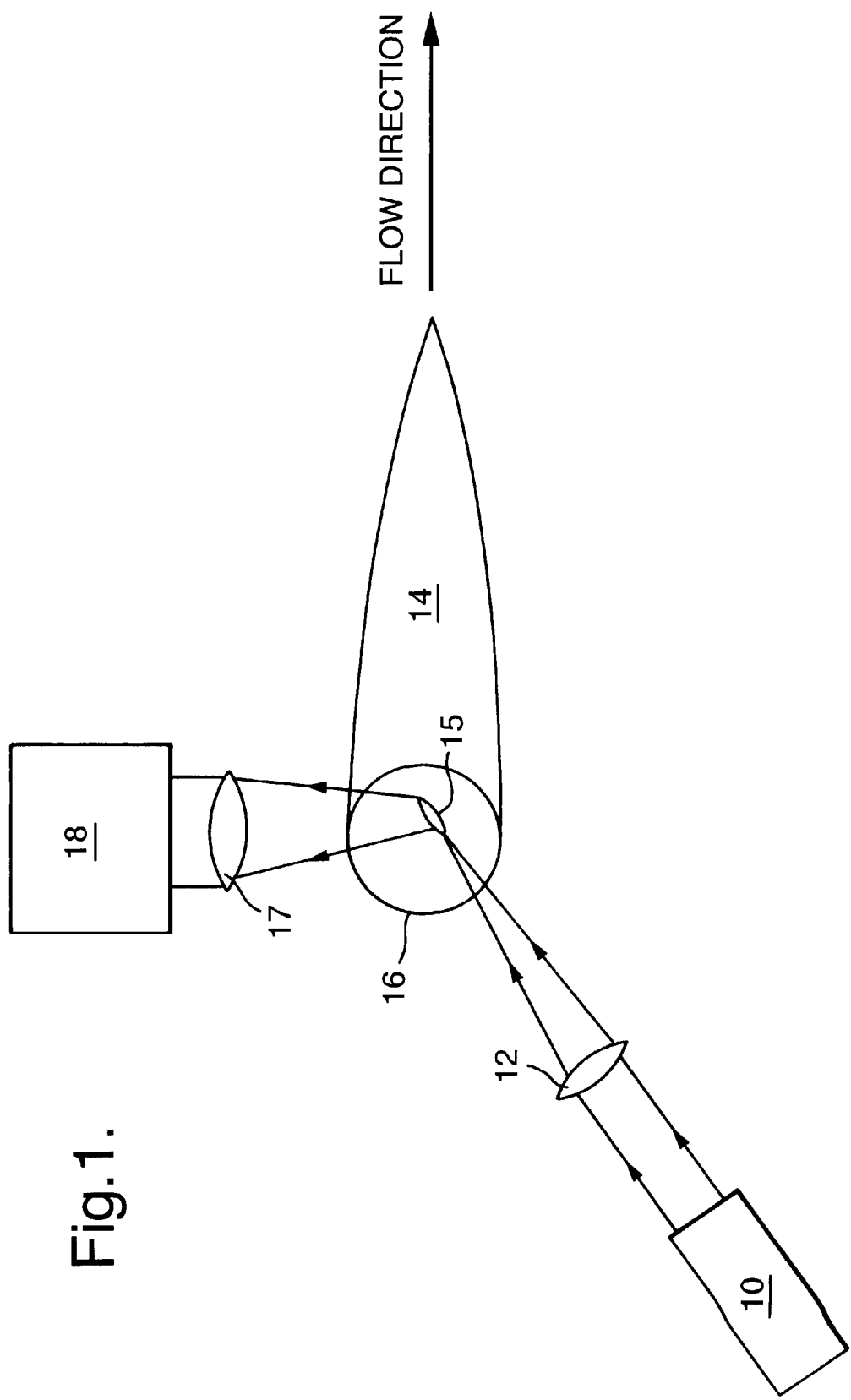
FIG. 1 is a schematic view of an optical arrangement suitable for use in fluid diagnostic techniques in accordance with the present invention.

With reference to FIG. 1, a high power laser 10, such as a Q-switched Neodymium/YAG laser, is focused by a lens 12 in a small volume of gas. The gas around the focus is ionised and a laser induced (dielectric) breakdown spark 15 is generated in the gas volume.

In the preferred embodiment of the present invention a Q-switched Neodymium/YAG laser 10 is used which has a pulse energy of approximately 300 mJ in 10 ns long pulses. The pulse of laser energy emitted by the laser 10 is focused by a 127 mm focal length lens 12 to generate the laser induced breakdown spark 15 in the gas volume.

The Q-switched Neodymium/YAG laser 10 produces the laser induced breakdown spark 15 in an air jet 14 emerging from a 37 mm diameter nozzle 16 at ambient temperature. However it will be appreciated by one skilled in the art that the arrangement described could be used to produce laser induced breakdown sparks in other media liquid or gaseous. Indeed the arrangement described has been used to generate laser induced breakdown sparks in an atmospheric pressure propane flame.

Images of the breakdown spark generated in the air jet were recorded using a gated intensified CCD camera 18 produced by Princeton instruments. A 105 mm focal length camera lens 17 stopped down to F/22 with appropriate extension tubes was used to image the spark on the CCD camera 18. A gate width of 100 ns was used with the intensifier gain on its minimum setting. With the air flow on, images were taken at each condition with the laser pulse in the center of the 100 ns detector gate and then with the gate delayed by 4.5 $\mu$s.

The delayed image which is due to the persistent light emitting species is shifted in the direction of the flow relative to the initial synchronous image. The shift in the center of the images was measured to enable the velocity of the fluid flow to be calculated.

FIG. 2 shows examples of the images recorded, the laser beam direction is from top to bottom. The intensifier is not sensitive to 1064 nm light, hence only the visible emissions and not the scattered light from the initial spark are recorded. Light emitting species can be seen diffusing from the position of the original spark up to 9.5 $\mu$s after the laser pulse.

FIG. 3 shows the velocities estimated from laser induced breakdown images plotted against values estimated from the air mass flow using equation (1);

$$\text{Velocity} = u = (dM/dt)/pA \qquad (1)$$

where dM/dt is the mass flow.

A is the nozzle area p is the air density outside the nozzle.

From FIG. 3 it can be seen that the relation holds for subsonic velocities. The measured velocities are close to the predicted values at three subsonic points in FIG. 3. As velocity is obtained from the measurement of an image shift which increases with velocity, the accuracy and resolution of the method should improve at higher velocities.

This velocimetry technique offers the advantages that it is non-intrusive, requires no particle or molecular seeding and is particularly suited to high speed flows.

As well as shifting downstream with time, the image also becomes larger due to diffusion of the excited, light emitting molecules. Temperature measurements can be obtained for a static flow by comparing the rate of increase of the light emitted from the delayed image to the synchronous image of the laser induced breakdown spark.

Laser induced breakdown is a simple non-intrusive technique which has been demonstrated for velocimetry and temperature measurement. The technique also has the potential for simultaneous species concentration and pressure measurement.

I claim:

1. A fluid diagnostic technique comprising the steps of:
    focusing a laser in the fluid to generate a laser induced breakdown spark;
    measuring the characteristics of the initial laser induced breakdown spark; and
    comparing the characteristics of the initial laser induced spark to the characteristics of a delayed image of the spark formed by light emission due to a recombination and excited molecules and ions generated by the laser induced spark, differences between the initial spark and the delayed image of the spark being used to diagnose characteristics of the fluid.

2. A fluid diagnostic technique for measuring the velocity of a fluid flow comprising the steps of:
    focusing a laser in the fluid to generate an initial laser induced breakdown spark;
    measuring a center of the initial laser induced breakdown spark; and
    comparing the center of the initial spark to a center of a delayed image of the spark formed by light emission due to recombination and excited molecules and ions generated by the initial laser induced spark, the shift in position of the center of the initial spark and the center of the delayed image of the spark being used to calculate the velocity of the fluid flow.

3. A fluid diagnostic technique for measuring the temperature of a fluid comprising the steps of focusing a laser in a fluid to generate an initial laser induced breakdown spark, comparing the initial laser induced breakdown spark to a delayed image of the spark formed by the light emission due to recombination and excited molecules and ions generated by the initial laser breakdown spark, the rate of increase of the light emitting volume around the delayed image being used to calculate the temperature of the fluid.

4. A fluid diagnostic technique as claimed in claim 1 in which a laser beam from a high power Neodymium/YAG laser is used to generate the laser induced breakdown spark.

5. A fluid diagnostic technique as claimed in claim 1 in which the laser beam is focused with a lens to generate the laser induced breakdown spark.

6. A fluid diagnostic technique as claimed in claim 1 in which a camera is used to record an image of the laser induced breakdown spark and the delayed image of the spark so that the images can be compared.

7. A fluid diagnostic technique as claimed in claim 1 in which a collection lens at 90° to the laser beam is used to collect light emitted by the laser induced breakdown spark.

8. A fluid diagnostic technique as claimed in claim 1 in which the initial spark and the delayed image of the spark are separated by a time interval of the order of 4.5 µs.

9. A fluid diagnostic technique as claimed in claim 2 in which a laser beam from a high power Neodymium/YAG laser is used to generate the laser induced breakdown spark.

10. A fluid diagnostic technique as claimed in claim 2 in which the laser beam is focused with a lens to generate the laser induced breakdown spark.

11. A fluid diagnostic technique as claimed in claim 2 in which a camera is used to record an image of the laser induced breakdown spark and the delayed image of the spark so that the images can be compared.

12. A fluid diagnostic technique as claimed in claim 2 in which a collection lens at 90° to the laser beam is used to collect light emitted by the laser induced breakdown spark.

13. A fluid diagnostic technique as claimed in claim 2 in which the initial spark and the delayed image of the spark are separated by a time interval of the order of 4.5 µs.

14. A fluid diagnostic technique as claimed in claim 3 in which a laser beam from a high power Neodymium/YAG laser is used to generate the laser induced breakdown spark.

15. A fluid diagnostic technique as claimed in claim 3 in which the laser beam is focused with a lens to generate the laser induced breakdown spark.

16. A fluid diagnostic technique as claimed in claim 3 in which a camera is used to record an image of the laser induced breakdown spark and the delayed image of the spark so that the images can be compared.

17. A fluid diagnostic technique as claimed in claim 3 in which a collection lens at 90° to the laser beam is used to collect light emitted by the laser induced breakdown spark.

18. A fluid diagnostic technique as claimed in claim 3 in which the initial spark and the delayed image of the spark are separated by a time interval of the order of 4.5 µs.

* * * * *